(12) United States Patent
Fischer et al.

(10) Patent No.: US 6,906,228 B2
(45) Date of Patent: Jun. 14, 2005

(54) METHOD FOR CATALYTIC HYDROGENATION ON RHENIUM-CONTAINING ACTIVE CARBON CARRIER CATALYSTS

(75) Inventors: Rolf Hartmuth Fischer, Heidelberg (DE); Rolf Pinkos, Bad Dürkheim (DE); Stephan Andreas Schunk, Heidelberg (DE); Joachim Wulff-Döring, Frankenthal (DE); Frank Stein, Bad Dürkheim (DE); Thomas Nöbel, Limburgerhof (DE); Sylvia Huber, Zwingenberg (DE)

(73) Assignee: BASF AG, Ludwigshafen (DE)

( * ) Notice: Subject to any disclaimer, the term of this patent is extended or adjusted under 35 U.S.C. 154(b) by 0 days.

(21) Appl. No.: 10/220,566

(22) PCT Filed: Mar. 1, 2001

(86) PCT No.: PCT/EP01/02337

§ 371 (c)(1),
(2), (4) Date: Oct. 29, 2002

(87) PCT Pub. No.: WO01/64338

PCT Pub. Date: Sep. 7, 2001

(65) Prior Publication Data

US 2003/0114719 A1 Jun. 19, 2003

(30) Foreign Application Priority Data

Mar. 1, 2000 (DE) .......................... 100 09 817

(51) Int. Cl.$^7$ .................. C07C 29/136; C07C 29/14; C07C 29/141; C07C 29/143; C07C 29/145; C07C 29/146; C07C 29/147; C07C 29/148; C07C 29/149

(52) U.S. Cl. .................. 568/883; 568/861; 568/862; 568/876; 568/814; 568/878; 568/880; 568/881; 568/884; 568/885; 568/864; 502/183; 502/182; 502/184

(58) Field of Search .................. 568/862, 861, 568/876, 814, 878, 880, 881, 883, 884, 885, 864; 502/183, 184; 522/182

(56) References Cited

U.S. PATENT DOCUMENTS

| 4,659,686 A | * | 4/1987 | Griffiths et al. ............. 502/183 |
| 5,302,765 A | | 4/1994 | Manzer et al. ............. 570/123 |
| 5,473,086 A | | 12/1995 | Budge et al. ............. 549/509 |
| 5,478,952 A | | 12/1995 | Schwartz .................. 549/325 |
| 5,698,749 A | | 12/1997 | Pedersen et al. ............ 568/864 |

FOREIGN PATENT DOCUMENTS

| EP | 0 276 012 | 7/1988 |
| EP | 0 848 991 | 6/1998 |
| EP | 0 881 203 | 12/1998 |
| GB | 1 551 741 | 8/1979 |

OTHER PUBLICATIONS

Derwent Chemical Abstract 95: 80602 X.
Jnl. Organic Chemistry vol. 24 (1959) pp. 1847–1854.

* cited by examiner

*Primary Examiner*—Elvis O. Price
(74) *Attorney, Agent, or Firm*—Novak Deuce & Quigg, LLP

(57) ABSTRACT

In a process for preparing alcohols by catalytic hydrogenation of carbonyl compounds over a catalyst comprising rhenium on activated carbon, the catalyst used comprises rhenium (calculated as metal) in a weight ratio to the activated carbon of from 0.0001 to 0.5, platinum (calculated as metal) in a weight ratio to the activated carbon of from 0.0001 to 0.5 and, if appropriate, at least one further metal selected from among Zn, Cu, Ag, Au, Ni, Fe, Ru, Mn, Cr, Mo, W and V in a weight ratio to the activated carbon of from 0 to 0.25, and the activated carbon has been nonoxidatively pretreated It is also possible to prepare ethers and lactones if the hydrogen pressure is not more than 25 bar. In this case, the activated carbon in the catalyst may also have been nonoxidatively pretreated.

8 Claims, No Drawings

METHOD FOR CATALYTIC HYDROGENATION ON RHENIUM-CONTAINING ACTIVE CARBON CARRIER CATALYSTS

The present invention relates to a process for the hydrogenation of compounds containing carbonyl groups over Re-containing, sometimes nonoxidatively pretreated catalysts supported on activated carbon for preparing alcohols while avoiding the formation of ethers, or for preparing ethers and lactones, with the preparation of the desired product being able to be controlled selectively The industrial preparation of alcohols frequently starts out from starting materials containing carbonyl groups, for example aldehydes, ketones, carboxylic acids, carboxylic anhydrides and esters, which are hydrogenated by means of hydrogen, The preparation of ethers and lactones frequently starts out from carboxylic acids, esters or anhydrides thereof, lactones or mixtures thereof.

In the recent past, particularly active catalysts using oxidatively pretreated activated carbon supports which have been oxidatively pretreated have been found. EP-A-0 848 991 describes a palladium-, silver-, rhenium- and iron-containing catalyst which, for example, can hydrogenate maleic acid or its esters to give bulanediol. In the hydrogenation of maleic acid at from 100 to 162° C., a selectivity to butanediol of 89.5% is achieved. However, the formation of 5.6% of tetrahydrofuran (THF) as ether by-product detracts from the success of the hydrogenation. In addition, 4% of n-butanol is formed as farther by-product.

U.S. Pat. No. 5,698,749 describes catalysts comprising an element of group VIII and additionally at least rhenium, tungsten or molybdenum on an oxidatively pretreated carbon support. In particular, Pd/Re/C or Pd/Re/Ag/C catalysts are described. Once again, THF is formed in addition to butanediol when using these catalysts in the hydrogenation of aqueous maleic acid. Here, butanediol is obtained in a selectivity of up to 92.8%, but THF is still formed in an amount of 1.6% and the further by-product n-butyl is formed in an amount of 4.6%.

The tendency of the hydrogenation metals rhenium or platinum to form THF and thus an ether in the hydrogenation of maleic acid derivatives is known (cf., for example, A. F. Timofeev et al., Prikl. Khim (Leningrad) 1981, 54(2), 335-8, Chemical Abstracts 95: 80602 X. The same effect is also described in GB-A-1 551 741 for the use of supported Pd/Re, Pt/Re or Pt/Pd/Re catalysts.

H. S. Broadbent et al., in J. Org. Chem. 24, 1847–1854 (1959) describe the hydrogenation of succinic acid over unsupported metallic Re, in which considerable amounts of THF are formed.

The avoidance of ethers as by-product is, however, desirable in industrial hydrogenation processes for preparing alcohols since their formation adversely affects the economics of the process. Furthermore, the ethers are sometimes difficult to separate from the desired product. The ethers also result in considerable disposal costs. THF, for example, is difficult to degrade biologically and must therefore no longer be introduced, even in small amounts, into a water treatment plant.

U.S. Pat. No. 5,478,952 relates to the hydrogenation of maleic acid over an Ru/Re activated carbon catalyst to form THF and gamma-butyrolactone as main products.

EP-A-0 276 012 relates to the hydrogenation of maleic acid to gamma-butyrolactone and butanediol over Pd/Re/TiO$_2$ catalysts.

Owing to the high corrosivity of acid solutions at high temperatures and pressures, it is desirable to carry out the hydrogenation at low temperatures.

It is an object of the present invention to provide rhenium catalysts by means of which carbonyl compounds can either be hydrogenated to alcohols with high overall selectivity, without ethers being formed, or can be hydrogenated selectively to ethers and lactones.

We have found that this object is achieved by a process for the catalytic hydrogenation of carbonyl compounds over a catalyst comprising rhenium on activated carbon, wherein the catalyst used comprises rhenium (calculated as metal) in a weight ratio to the activated carbon of from 0.0001 to 0.5, platinum (calculated as metal) in a weight ratio to the activated carbon of from 0.0001 to 0.5 and, if appropriate, at least one further metal selected from among Zn, Cu, Ag, Au, Ni, Fe, Ru, Mn, Cr, Mo, W and V in a weight ratio to the activated carbon of from 0 to 0.25, for preparing alcohols, in which case the activated carbon has been nonoxidatively pretreated, or for preparing ethers and lactones, in which case the starting substances are carboxylic acids, esters or anhydrides thereof, lactones or mixtures thereof, the hydrogenation is carried out at a hydrogen pressure of not more than 25 bar and the activated carbon may have been nonoxidatively pretreated.

It has been found that carbonyl compounds can be hydrogenated catalytically to give the corresponding alcohols without ether formation at low temperatures (preferably below 140° C.) when at least rhenium or rhenium/platinum on nonoxidatively pretreated carbon supports such as activated carbon are used for the hydrogenation.

In the present context, the expression "without ether formation" means that any ether formed should make up not more than 0.5% of the hydrogenation products. The ether content is preferably below 0.2%, particularly preferably below 0.1%.

At low pressures, the preparation of ethers and lactones, generally in admixture, is possible. The reaction can be controlled and directed at the desired products by means of the hydrogen pressure, with predominantly alcohols being formed at relatively high pressures and predominantly ethers and lactones being formed at low pressures. In this way, ethers can be formed as main products.

A nonoxidative treatment of the carbon support material with mineral acids or bases is advantageous compared to an oxidative treatment with HNO$_3$ or peroxides since an oxidative pretreatment of activated carbon with H$_2$O$_2$ or peroxides represents an expensive pretreatment process which considerably increases the catalyst manufacturing costs. The oxidative pretreatment with HNO$_3$ results in formation of nitrous gases which have to be removed in complicated waste gas purification processes (DeNOX). A further disadvantage of oxidative pretreatment is the material loss of support material caused by the oxidative pretreatment. The carbon-containing support materials partly dissolve in the oxidizing agents and shaped bodies can even disintegrate completely if the temperature is too high.

As activated carbon, commercially available activated carbons are generally suitable. Preference is given to using ones which contain little chlorine and sulfur and whose proportion of micropores relative to the proportion of mesopores and macropores is very low. The nonoxidative treatment of the activated carbon can in the simplest case be carried out by treatment with solvents such as water or alcohols. The carbon support can also be conditioned by nonoxidative treatment with mineral acids such as HCl, H$_3$PO$_4$, H$_2$SO$_4$, HBr or HF. Organic acids such as formic acid or acetic acid can also be used for the pretreatment of the support material. Carbon supports which have been treated with solutions of bases such as NH$_4$OH, NaOH or KOH likewise have a positive effect on the catalytic performance.

The treatment of the activated carbon with the nonoxidizing treatment agent can be carried out before or during the application of the platinum and rhenium components or further catalyst components.

In a further particular embodiment, use is made of catalysts in which the activated carbon support is firstly pretreated nonoxidatively and is then pretreated oxidatively. In a further particular embodiment, use is made of catalysts in which the activated carbon support is firstly pretreated oxidatively and is then pretreated nonoxidatively.

In a preferred nonoxidative pretreatment, the activated carbon support is stirred in the pretreatment agent at elevated temperature (50–90° C.). As pretreatment agents, it is possible to use either concentrated or dilute pretreatment agents (acids, alkalis). Preference is given to using concentrated pretreatment agents (conc. HCl, conc. NaOH, half strength $H_3PO_4$). The treatment time is generally in the range from 1 to 48 hours, preferably from 5 to 30 hours. After the treatment, the carbon support is freed of interfering ions by washing with water. An after-treatment in water at elevated temperature (for from 1 to 48 hours, preferably from 5 to 30 hours) can follow.

When acidic pretreatment agents are used, a pH test (5 g of carbon support boiled in distilled $H_2O$ for 20 minutes, solution filtered, allowed to cool under nitrogen, pH measured at 20° C.) indicates a more acidic surface than in the case of the starting material, while the use of basic pretreatment agents results in a more basic surface.

As rhenium component, use is usually made of $(NH_4)ReO_4$, $Re_2O_7$, $ReO_2$, $ReCl_3$, $ReCl_5$, $Re(CO)_5Cl$, $Re(CO)_5Br$ or $Re_2(CO)_{10}$, without this listing being intended to be exclusive. Preference is given to using $Re_2O_7$.

Apart from rhenium, platinum is also applied to the catalyst. The platinum can be applied as, for example, platinum powder, oxide, hydrated oxide, nitrate, platinum (II) or (IV) chloride, hexachloroplatinic(IV) acid, platinum (ID or (IV) bromide, platinum(II) iodide, cis- or trans-diammineplatinum(II) chloride, cis- or trans-diammineplatinum(IV) chloride, diammineplatinum(II) nitrite, (ethylenediamine)platinum(II) chloride, tetrammineplatinum(II) chloride or chloride hydrate, tetrammineplatinum(II) nitrate. (ethylenediamine)platinum (II) chloride, tetrakis(triphenylphosphine)platinum(0), cis- or trans-bis(triethylphosphine)platinum(II) chloride, cis- or trans-bis(triethylphosphine)platinum(II) oxalate, cis-bis (triphenylphosphine)platinum(II) chloride, bis (triphenylphosphine)-platinum(IV) oxide, (2,2'-6',2"-terpyridine)platinum(IT) chloride dihydrate, cis-bis (acetonitrile)platinum dichloride, cis-bis(benzonitrile) platinum dichloride, platinum(II) acetylacetonate, (1c,5c-cyclooctadiene)platinum(II) chloride or bromide, platinum nitrosyl nitrate, preferably as platinum oxide or nitrate, particularly preferably as platinum nitrate, without this listing being intended to be exclusive.

Rhenium (calculated as metal) can be applied in a weight ratio to the activated carbon of from 0.0001 to 0.5, preferably from 0.001 to 0.2, particularly preferably from 0.01 to 0.15. The same ratios apply for platinum. The weight ratio of rhenium to platinum (calculated as metals) is in the range from 0.01 to 100, preferably from 0.05 to 50, particularly preferably from 0.1 to 10.

Further elements can additionally be present on the catalyst. Examples which may be mentioned are Zn, Cu, Ag, Au, Ni, Fe, Ru, Mn Cr, Mo, W and V. These elements modify the catalyst essentially in respect of activity and selectivity (hydrogenolysis products), but are not absolutely necessary. Their weight ratio to Re can be from 0 to 100, preferably from 0.5 to 30, particularly preferably from 0.1 to 5.

The application of the active components Re and Pt can be carried out by impregnation in one or more steps with an aqueous or alcoholic solution or solution in other organic solvents of the respective salts impregnation with a solution of an oxidic or metallic colloid of the active components, equilibrium adsorption in one or more steps of the salts dissolved in aqueous or alcoholic solution or equilibrium adsorption of dissolved metallic or oxidic colloid on the pretreated activated carbon. In these methods, the active components can be applied to the activated carbon either simultaneously or in succession A drying step for removal of the solvent is carried out between each of the individual impregnation or equilibrium adsorption steps. The active components are preferably applied by impregnation with an aqueous salt solution or an aqueous oxidic colloid in one step.

To remove the solvent after the impregnation or equilibrium adsorption step, the impregnated catalyst is dried. The drying temperature is 30–350° C., preferably 40–280° C., particularly preferably 50–150° C.

The catalysts are usually activated before use. This activation can be achieved by allowing a reducing gas atmosphere to act on the catalyst. Activation by means of hydrogen is preferably employed. The activation temperature is usually 100–500° C., preferably 130–400° C., particularly preferably 150–350° C. Alternative reduction methods are reduction of the metallic components by bringing the catalyst into contact with a liquid reducing agent such as hydrazine, formaldehyde or sodium formate. Here, the liquid reducing agents are usually brought into contact with the catalyst at from 10 to 100° C., particularly preferably from 20 to 80° C.

The hydrogenation for preparing alcohols is usually carried out at 50–250° C., preferably 60–220° C., particularly preferably 70–190° C., very particularly preferably 80–140° C. The hydrogenation is usually carried out at a reaction pressure in the range from 3 to 330 bar, preferably from 20 to 300 bar. The pressure of the hydrogenation in the liquid phase over a fixed bed is preferably above 150 bar, more preferably 150–300 bar, in the gas phase over a fixed bed it is preferably from 3 to 100 bar and in suspension it is preferably from 10 to 90 bar.

Suitable starting materials for the hydrogenation for preparing alcohols are carbonyl compounds in general, which may additionally contain C—C double or triple bonds. Examples of aldehydes are propionaldehyde, butyraldehyde, crotonaldehyde, ethylhexanal, nonanal and glucose. Examples of carboxylic acids are succinic acid, fumaric acid, maleic acid, glutaric acid, adipic acid, hydroxycaproic acid, octanedioic acid, dodecanedioic acid, 2-cyclododecylpropionic acid and saturated or unsaturated fatty acids. Esters which may be mentioned are esters of the abovementioned acids, for example methyl, ethyl, propyl or butyl esters; lactones such as gamma-butyrolactone, delta-valerolactone or caprolactone can also be used. Furthermore, it is possible to use anhydrides such as succinic anhydride or maleic anhydride. Preferred starting materials are succinic acid, maleic acid, adipic acid, 2-cyclododecylpropionic acid, succinic anhydride, maleic anhydride and esters of these acids and gamma-butyrolactone.

For the preparation of ethers and lactones, it has been found that, in particular, $C_4$–$C_5$-dicarboxylic acids, -dicarboxylic esters and dicarboxylic anhydrides can be hydrogenated catalytically to give primarily the corresponding cyclic ethers and lactones as further components of value at low hydrogen pressures ($\leq 25$ bar, preferably $\leq 20$ bar) when at least rhenium and platinum on carbon supports such as activated carbon are used for the hydrogenation.

Only gamma-butyrolactone (GBL) has hitherto been obtained at similarly low pressures. A further considerable disadvantage has hitherto been an incomplete acid conversion at such low pressures. These disadvantages are now overcome.

The hydrogenation is preferably carried out at from 50 to 250° C., preferably from 60 to 240° C., particularly preferably from 70 to 235° C.

The cyclic ethers and lactones obtained in the process of the present invention are used, for example, as solvents and intermediates. A treatment of the carbon support material can also be carried out for the preparation of ethers and lactones, but is not absolutely necessary.

Suitable starting materials for the hydrogenation for preparing ethers and lactones are carbonyl compounds in general, which may additionally contain C—C double or triple bonds. Examples of carboxylic acids are succinic acid, fumaric acid, maleic acid, glutaric acid, adipic acid, hydroxycaproic acid. Suitable esters are esters of the above-mentioned acids, for example the methyl, ethyl, propyl or butyl esters; it is also possible to use lactones, for example γ-butyrolactone, δ-valerolactone or caprolactone. Anhydrides such as succinic anhydride or maleic anhydride can also be used. Preferred starting materials are succinic acid, maleic acid, adipic acid, succinic anhydride, maleic anhydride and the esters of these acids and γ-butyrolactone. Particular preference is given to hydrogenating maleic acid, fumaric acid, succinic acid or esters or anhydrides thereof or gamma-butyrolactone to form THF and gamma-butyrolactone.

The compounds to be hydrogenated can be hydrogenated in bulk or in solution. Possible solvents are, for example, the hydrogenation product itself or substances which are inert under the reaction conditions, e.g. alcohols such as methanol, ethanol, propanol or butanol or ethers such as THF or ethylene glycol ethers. A preferred solvent is water, particularly in the hydrogenation of carboxylic acids.

The hydrogenation can be carried out in the as or liquid phase, in one or more stages. In the liquid phase, both the suspension mode and the fixed-bed mode are possible. In the case of exothermic reactions, the heat can be removed by means of external coolants (e.g. shell-and-tube reactor). Evaporative cooling in the reactor is also possible, especially when the hydrogenation is carried out without product recycle. In the case of product recycle, a cooler in the recycle stream is a possibility.

The alcohols obtained in the process of the present invention are used, for example, as solvents and intermediates. Diols such as butanediol are used as diol component in polyesters. 2-Cyclododecylpropan-1-ol is a sought-after musk fragrance.

The process of the present invention is illustrated by the following examples. The contents of the individual components reported for the hydrogenation products have been determined by gas chromatography. They are, unless indicated otherwise, calculated on a solvent-free basis.

EXAMPLES

Preparation of Alcohols

Example 1 (Comparison)

20 g of activated carbon (Epibon Spezial®, from Lurgi) were oxidatively pretreated using 95% strength $H_2SO_4$, impregnated with 5 g of $Re_2O_7$ and 15 g of platinum nitrate solution (=2.5 g of $PtO_2$) and dried. The further procedure was as follows: for 30% strength maleic acid solution, a reaction temperature of about 155° C. and a total time of 78 hours, about 94% of butanediol and 5.26% of n-butanol, 0.31% of propanol, 0.3% of methanol and 0.3% of THF were found in the product, Example 2 (Comparison)

Using a method analogous to Example 1, 20 g of activated carbon (BG 09®, from Jacobi) were oxidatively pretreated using 44% strength $H_2SO_4$, impregnated with 5 g of $Re_2O_7$ and 15 g of platinum nitrate solution (2.5 g of $PtO_2$) and dried. The further procedure was as in Example 1. For 30% strength maleic acid solution, a reaction temperature of about 141° C. and a total time of 78 hours, about 76.63% of butanediol and 20.53% of n-butanol, 1.84% of propanol, 0.52% of methanol and 0.49% of THF were found in the product.

Example 3

Using a method analogous to Example 1, 20 g of activated carbon (BG 09®, from Jacobi) were nonoxidatively pretreated using 1 M NaOH, impregnated with 5 g of $Re_2O_7$ and 15 g of platinum nitrate solution (=2.5 g of $PtO_2$) and dried. The further procedure was as in Example 1. For 30% strength maleic acid solution, a reaction temperature of about 122° C. and a total time of 78 hours, about 88.92% of butanediol and 10.77% of n-butanol, 0.3% of propanol and no THF were found in the product.

Example 4

Using a method analogous to Example 1, 20 g of activated carbon (BG 09®, from Jacobi) were nonoxidatively pretreated using concentrated HCl, impregnated with 5 g of $Re_2O_7$ and 15 g of platinum nitrate solution (=2.5 g of $PtO_2$) and dried. The further procedure was as in Example 1. For 30% strength maleic acid solution, a reaction temperature of about 114° C. and a total time of 78 hours, about 92.13% of butanediol and 7.87% of n-butanol and no THF were found in the product.

Example 5

Using a method analogous to Example 1, 20 g of activated carbon (BG 09®, from Jacobi) were nonoxidatively pretreated using steam and subsequently 5% strength HCl, impregnated with 5 g of $Re_2O_7$ and 15 g of platinum nitrate solution (=2.5 g of $PtO_2$) and dried. The further procedure was as in Example 1. For 30% strength maleic acid solution, a reaction temperature of about 131° C. and a total time of 78 hours, about 91.4% of butaiediol and 8.26% of n-butanol, 0.32% of propanol and no THF were found in the product.

Example 6

Using a method analogous to Example 1, 20 g of activated carbon (BG 09®, from Jacobi) were nodoxidatively pretreated using 44% strength $H_3PO_4$, impregnated with 5 g of $Re_2O_7$ and 15 g of platinum nitrate solution (=2.5 g of $PtO_2$) and dried. The further procedure was as in Example 1. For 30% strength maleic acid solution, a reaction temperature of about 107° C. and a total time of 78 hours, about 93.36% of butanediol and 5.86% of n-butanol, 0.21% of methanol and no THF were found in the product.

Catalysts produced by nonoxidative treatment of the activated carbon were able to hydrogenate maleic acid to the target product 1,4-butanediol at a lower temperature than the known catalysts. In addition, the proportion of ether by-product could be greatly reduced.

Preparation of Ethers and Lactones

Example 1

60 g of activated carbon (Epibon from Lurgi) were pretreated with phosphoric acid and dried at 120° C. 50 g of the carbon which had been pretreated in this way were impregnated with 9.81 g of Pt(NO$_3$)$_2$ as an aqueous solution. The impregnated activated carbon was dried at 110° C. for 18 hours, subsequently reduced in a stream of nitrogen/hydrogen at 300° C. and ambient pressure for 4 hours and passivated at room temperature in a stream of nitrogen/air. The passivated catalyst was subsequently impregnated with 5 g of Re$_2$O$_7$ and dried at 110° C. for 18 hours. The catalyst obtained in this way was activated in a stream of nitrogen/hydrogen at 300° C. and ambient pressure for 4 hours and passivated at room temperature in a stream of nitrogen/air. The reduced catalyst contains 3% of Pt and 3% of Re. 25 ml of the activated/passivated catalyst were subsequently placed in a reactor having a capacity of 25 ml.

The hydrogenation was carried out in the downflow mode, without product recirculation. The reaction pressure was 20 bar and about 180 standard l/h of hydrogen were fed in. At a maleic acid concentration of 30% (water), an LHSV of 0.1 h$^{-1}$ and a reactor temperature of 235° C., the hydrogenation product comprised about 73.5% of THF, 1.3% of GBL, 0% of BDO and 25.0% of alcohols (n-butanol+n-propanol) after a total of 3 hours. The acid conversion was 95.3%. At an LHSV of 0.2 h$^{-1}$ but otherwise identical conditions, a hydrogenation product comprising about 36.5% of THF, 42.7% of GBL, 0.90% of BDO and 19.8% of alcohols (n-butanol+n-propanol) was obtained after a time of 17.5 h. The acid conversion was 95.1%.

Example 2 (Reference)

60 g of activated carbon (Epibon from Lurgi) were pretreated with phosphoric acid and dried at 120° C. 50 g of the carbon which had been pretreated in this way were impregnated with 2.5 g of PdCl$_2$ as an aqueous solution. The impregnated activated carbon was dried at 110° C. for 18 hours, subsequently reduced in a stream of nitrogen/hydrogen at 300° C. and ambient pressure for 4 hours and passivated at room temperature in a stream of nitrogen/air. The passivated catalyst was subsequently impregnated with 5 g of Re$_2$O$_7$ and dried at 100° C. for 18 hours. The catalyst obtained in this way was activated in a stream of nitrogen/hydrogen at 300° C. and ambient pressure for 4 hours and passivated at room temperature in a stream of nitrogen/air. The reduced catalyst contains 3% of Pd and 3% of Re. 25 ml of the activated/passivated catalyst were subsequently placed in a reactor having a capacity of 25 ml.

The hydrogenation was carried out in the downflow mode, without product recirculation. The reaction pressure was 20 bar and about 100 standard l/h of hydrogen were fed in. At a maleic acid concentration of 30% (water), an LHSV of 0.1 h$_{-1}$ and a reactor temperature of 235° C., the hydrogenation product comprised about 65.2% of THF, 11.9% of GBL, 0% of BDO and 22.9% of alcohols (n-butanol+n-propanol) after a total of 3 hours. The acid conversion was 98.5%.

When using Pt/Re catalysts on activated carbon support materials, maleic acid can be hydrogenated at low hydrogen pressures to give predominantly the target product tetrahydrofuran and small proportions of gamma-butyrolactone as further product of value with high acid conversions and higher selectivities than those obtained using comparable Pd/Re activated carbon catalysts.

We claim:

1. A process for preparing alcohols by catalytic hydrogenation of carbonyl compounds over a catalyst comprising rhenium and platinum on nonoxidatively pretreated activated carbon, which has not been oxidatively pretreated, wherein rhenium (calculated as metal) is used in a weight ratio to the activated carbon of from 0.0001 to 0.5, platinum (calculated as metal) in a weight ratio to the activated carbon of from 0.0001 to 0.5 and, optionally, at least one further metal selected from among Zn, Cu, Ag, Au, Ni, Fe, Ru, Mn, Cr, Mo, W and V in a weight ratio to the activated carbon of from 0 to 0.25, wherein the activated carbon has been nonoxidatively pretreated with water vapor, nonooxidizing mineral acids or nonoxidizing organic acids or bases and the hydrogenation is carried out at a temperature in the range of from 80 to 140° C.

2. A process as claimed in claim 1, wherein the pretreatment of the activated carbon is carried out using HCl, H$_3$PO$_4$, formic acid, acetic acid, NH$_4$OH, NaOH or KOH.

3. A process as claimed in claim 1, wherein the hydrogenation is carried out in the liquid phase over fixed-bed catalysts at a pressure in the range from 150 to 300 bar.

4. A process as claimed in claim 1, wherein the hydrogenation is carried out in the liquid phase over fixed-bed catalyst at from 80 to 131° C.

5. The process of claim 1, wherein the hydrogenation products contain no more than 0.5% of ethers.

6. The process of claim 5 wherein the percentage of ethers is less than 0.1%.

7. The process of claim 1 wherein the activated carbon has been nonoxidatively treated with water vapor or nonooxidizing organic acids.

8. The process of claim 2 wherein the pretreatment of the activated carbon is carried out using HCl, H$_3$PO$_4$, formic acid, acetic acid or NH$_4$OH.

* * * * *